(12) United States Patent
Dahanukar et al.

(10) Patent No.: US 6,875,866 B2
(45) Date of Patent: Apr. 5, 2005

(54) PROCESS FOR SYNTHESIS OF D1 RECEPTOR ANTAGONISTS

(75) Inventors: Vilas H. Dahanukar, Edison, NJ (US); Jeffrey M. Eckert, Hazlet, NJ (US); Dinesh Gala, East Brunswick, NJ (US); Brian Lucas, Madison, WI (US); Doris P. Schumacher, Bedminster, NJ (US); Ilia Zavialov, East Windsor, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/368,973

(22) Filed: Feb. 19, 2003

(65) Prior Publication Data

US 2003/0199690 A1 Oct. 23, 2003

Related U.S. Application Data

(60) Provisional application No. 60/358,992, filed on Feb. 21, 2002.

(51) Int. Cl.$^7$ .............................................. C07D 223/14
(52) U.S. Cl. ...................................................... 540/576
(58) Field of Search .......................................... 540/576

(56) References Cited

U.S. PATENT DOCUMENTS

| | | | |
|---|---|---|---|
| 4,973,586 A | * 11/1990 | Berger et al. ................ | 514/215 |
| 5,463,051 A | * 10/1995 | Hou et al. .................... | 540/576 |
| 5,670,666 A | 9/1997 | Hou et al. .................... | 549/373 |

OTHER PUBLICATIONS

Berger, et al., 1989, *J. Med. Chem.*, 32:1913–1921.

Richard W. Draper, et al., Organic Process Research & Development, "Novel Stereoselective Syntheses of the Fused Benzazepine Dopamine D1 Antagonists (6as, 13br)–11–Chloro–6, 6a, 7, 8, 9, 13b–hexahydro–7–methyl–5H–benzol[d]naphtha[2,1–b] azepin–12–01(Sch 39166): 1. Aziridinium Salt Based Synthesis" 1998, 2 175–185.

* cited by examiner

*Primary Examiner*—Bruck Kifle
(74) *Attorney, Agent, or Firm*—William Y. Lee

(57) ABSTRACT

In one embodiment, the present invention describes the synthesis of a compound of formula

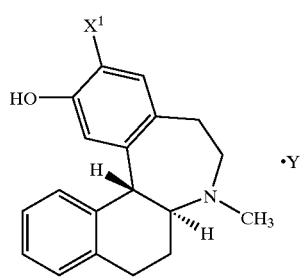

I and intermediates therefor.

20 Claims, No Drawings

PROCESS FOR SYNTHESIS OF D1 RECEPTOR ANTAGONISTS

This application claims the benefit of U.S. Provisional Application No. 60/358,992, filed Feb. 21, 2002.

BACKGROUND OF THE INVENTION

The present invention relates to a novel process for preparing benzazepines having activity as selective D1 receptor antagonists.

U.S. Pat. No. 4,973,586 discloses fused benzazepines as selective D1 antagonists useful in the treatment of psychoses, depression, pain and D1 dependent neurological disorders. Methods for preparing such compounds are also described therein. One disclosed fused benzazepine (ecopipam) has the structure:

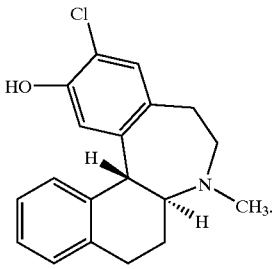

Berger, et al, *J. Med. Chem.*, 32, 1913–1921 (1989), discloses a process for preparing the above fused benzazepine comprising acid promoted cyclization of a compound of the formula (1) to give a 1:1 mixture of cis and trans benzazepines (cis-2 and trans-2, respectively). Compound trans-2 is then converted to the desired trans-2 benzazepine non-chiral compound I via a multi-step procedure. Compound I is resolved via its di-O,O'-p-tolyltartrate salt and hydrolyzed with HBr and HOAc to give the desired benzazepine compound.

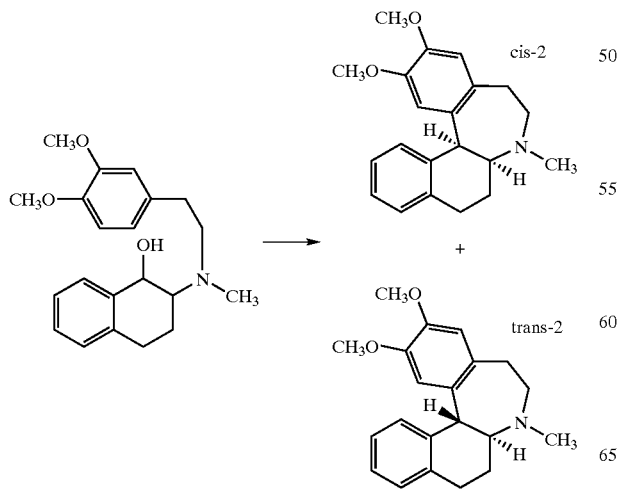

trans-2 -----> ----->

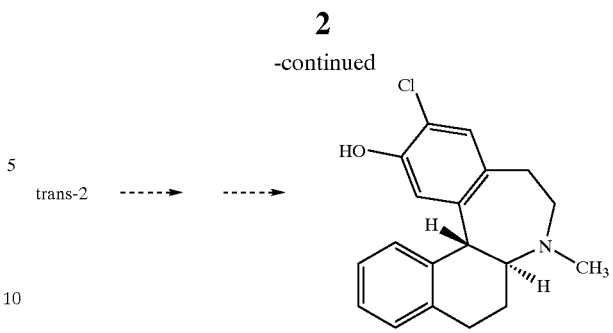

U.S. Pat. Nos. 5,463,051 and 5,670,666 disclose intermediates of the formulae

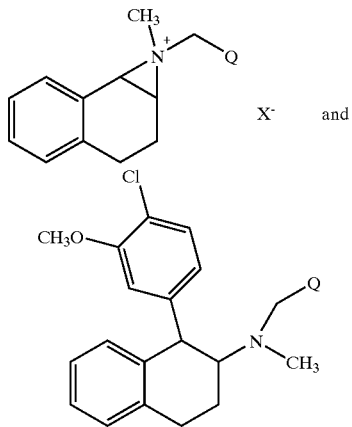

where $X^-$ is halide, $BF_4^-$, $R^3SO_3^-$, where $R^3$ is $C_1$–$C_6$ alkyl, $CF_3$, $C_1$–$C_1$–$C_6$ alkylphenyl or phenyl, and Q has the formula

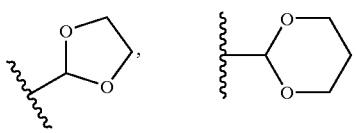

or —$CH(OR)_2$ where R is $C_1$–$C_6$ alkyl;

and a process for preparing benzazepine intermediates, one of which has the formula:

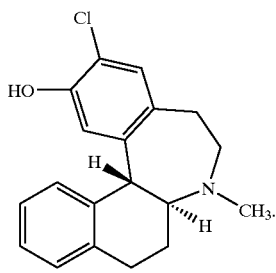

These benzazepine intermediates are useful for preparing benzazepines having activity as selective D1 receptor antagonists.

SUMMARY OF THE INVENTION

In one embodiment, the present application teaches a novel, simple process of making a compound of formula I and intermediates useful in said process of making a compound of formula I. The compound of formula I is shown below:

where $X^1$ is Cl or F and Y is selected from the group consisting of malonate, oxalate, sulfonate, phosphate and hydrochloride ions, is prepared from a compound of formula II:

where Q has the formula or —CH(OR)$_2$, where R is C$_1$–C$_6$ alkyl and wherein X is an anion selected from the group consisting of:
- halide ion,
- BF$_4^-$,
- CH$_3$C$_6$H$_4$SO$_3^-$,
- C$_6$H$_5$SO$_3^-$,
- CH$_3$SO$_3^-$,
- CF$_3$SO$_3^-$,
- PO$_4^-$,
- phosphonate of the formula (R$^1$O)$_2$P(O)O$^-$ where R$^1$ is an alkyl or aryl group, a group of the formula (OR$^1$)PO$^-$ where R$^1$ is an alkyl or aryl group, and a group of the formula (R$^2$)$_2$(O)PO$^-$, where R$^2$=OR, O-aryl, NR$_2$, and SR.

The process of making the compound of formula I from the compound of formula II comprises:

(a) reacting the compound of formula II with an organometallic reagent of formula III:

where $X^1$ is Cl or F, where M is selected from the group consisting of Co, Ni, Mg, Zn, Ti, Ce, Mn and Cu; and L is selected from the group consisting of Br, Cl, CN, acetate and acetyl acetate, p being a number ranging from 1 to 3 depending on the valence of M;

in the presence of a metal salt of the formula CuZ$_m$ (m is 1 or 2) or in the presence of a copper salt-lithium chloride complex of formula, CuZ$_n$·dLiCl (n is 1 or 2, d ranges from 1 to 4), where Z is selected from the group consisting of cyanide, halide, acetate, acetyl acetonate, benzoyl benzoate, trifluoroacetate, thiophenoxide, phenylacetylide, thiocyanate, tetrafluoroborate, trifluoromethanesulfonate and trifluoroacetylacetonate, followed by treatment with acid HY, to form a compound of formula IV:

where $X^1$ and Y are as defined above;

b) cyclizing and reducing the compound of formula IV to form a compound of formula V;

and (c) deprotecting the compound of formula V to form the compound of formula I.

DETAILED DESCRIPTION

In one embodiment, the present invention discloses a novel, easy-to-use process for preparing the compound of formula I. The inventive process is schematically described in Scheme I:

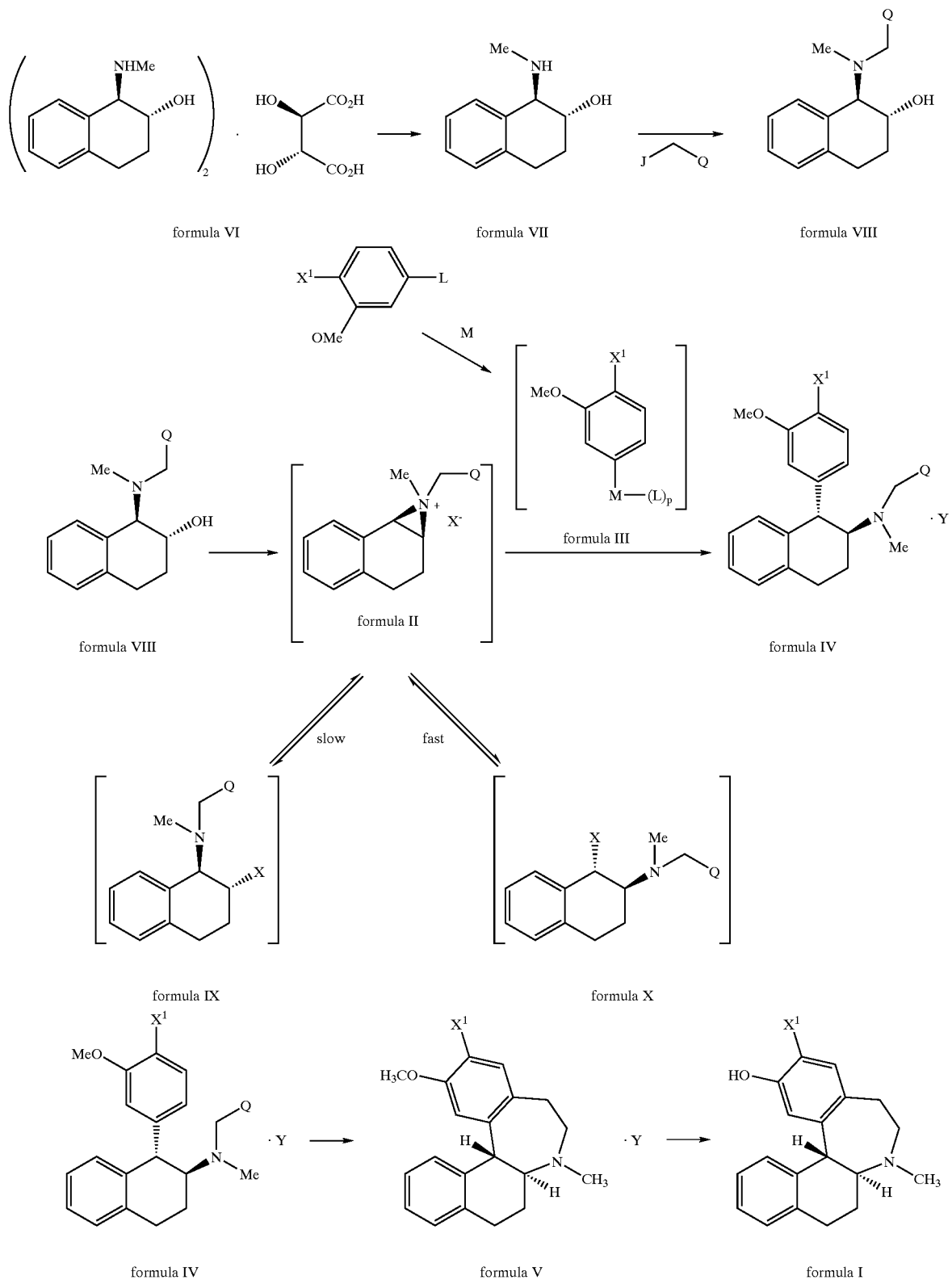
Scheme 1
The moieties Q, X, M and L are as defined above.

In general, stereochemical representations are meant to denote relative stereochemistry. However, where optically active starting materials are employed, the stereochemical representations denote absolute as well as relative stereochemistry. Therefore, by using such optically active starting materials, compounds of the formula I can be prepared as a single enantiomer. Similarly, by utilizing stereoselective transformations on prochiral compounds to generate chiral compounds, or by performing a resolution step, if necessary, a single enantiomer of compounds of the formula I is produced, i.e. no prochiral compounds.

In those embodiments where the present invention relates to chiral compounds, the stereochemical purity of such compounds is generally given in terms of the enantiomeric excess (e.e.).

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, and 3-methylbut-2-enyl.

"Aryl" means an aromatic monocyclic or multi-cyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. Non-limiting examples of suitable aryl groups include phenyl and naphthyl.

"Halo" means fluoro, chloro, bromo, or iodo groups. Preferred are fluoro chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Tertiary amine base" means a tertiary amine selected from pyridine, di-isopropylethylamine or a tri-($C_1$–$C_6$ alkyl) amine, such as triethylamine.

"Base" means compounds such as $NH_4OH$, $KHCO_3$, $K_2CO_3$, $NaHCO_3$, $Na_2CO_3$, NaOH, KOH or LiOH, or an alkaline earth metal hydroxide such as $Ca(OH)_2$.

"Leaving group" means a group which can be readily displaced by a nucleophile, preferably, but not limited to —Cl, —Br, —I, —OSO$_2$CH$_3$, —OSO$_2$CF$_3$ or —OSO$_2$C$_6$H$_4$CH$_3$, phosphate, phosphite or phosphonate.

"Alkyllithium" means an alkyllithium reagent, such as n-butyllithium, methyllithium, sec-butyllithium, hexyllithium or tert-butyllithium.

"Aziridinium forming reagent" means a reagent that forms an aziridinium group, said reagent containing a halophosphate, halophosphite, pyrophosphate, phosphoramidate, phosphorite, phosphate, phosphonate of the formula $(R^1O)_2P(O)O^-$ where $R^1$ is an alkyl or aryl group, a group of the formula $(OR^1)PO^-$ where $R^1$ is an alkyl or aryl group, and a group of the formula $(R^2)_2(O)PO^-$; where $R^2$=OR, O-aryl, NR$_2$, and SR, for example diphenyl chlorophosphate and/or diphenyl phosphoryl chloride.

"Acid" means a protic acid, such as $H_2SO_4$ or $CH_3SO_3H$, or a Lewis acid capable of catalyzing a Friedel-Crafts type reaction, such as AlCl$_3$.

"Deprotecting" means removal of a group from another group by a suitable reagent.

"Reducing agent" means, but is not limited to, a metal hydride reducing agent, such as NaBH$_4$, NaBH$_3$CN, LiBH$_4$ or LiAlH$_4$, or a borane amine complex, such as borane-methylamine, borane-tert-butylamine, borane-piperidine, borane-triethylamine, borane-N,N-diisopropylethylamine, borane-N,N-diethylaniline, borane-morpholine, borane-4-ethylmorpholine or borane-4-phenylmorpholine complex.

"Counterion" means an anion selected from a halide, BF$_4^-$, CH$_3$C$_6$H$_4$SO$_3^-$, C$_6$H$_5$SO$_3^-$, CH$_3$SO$_3^-$, CF$_3$SO$_3^-$, PO$_4^-$, phosphonate of the formula $(R^1O)_2P(O)O^-$ where $R^1$ is an alkyl or aryl group of the formula $(OR^1)PO^-$ where $R^1$ is an alkyl or aryl group, and a group of the formula $(R^2)_2(O)PO^-$, where $R^2$=OR, O-aryl, NR$_2$, and SR.

"Copper salts" means those copper salts CuZ$_m$ where (m is 1 or 2), Z is cyanide, a halide, acetate, acetyl acetonate, benzoyl benzoate, trifluoroacetate, thiophenoxide, phenylacetylide, thiocyanate, tetrafluoroborate, trifluoromethanesulfonate or trifluoroacetylacetonate or those copper salt-lithium chloride complexes of copper salts where, $CuZ_n \cdot dLiCl$ (n is 1 or 2, d ranges from 1 to 4) or where said copper salt can complex with lithium thienyl cyanocuprate.

As used herein the following reagents and solvents are identified by the abbreviations indicated: para-toluenesulfonyl chloride (tosyl chloride, TsCl); para-bromobenzenesulfonyl chloride (brosyl chloride); methanesulfonyl chloride (mesyl chloride, MsCl); tetrahydrofuran (THF); iso-propanol (i-PrOH); methanol (MeOH); ethyl acetate (EtOAc); borane-tert-butylamine complex ($BH_3 \cdot tBuNH_2$); triethylamine ($Et_3N$) and diethylene glycol dimethyl ether (diglyme).

The aziridinium salts of step (a) of the process of the present invention contain a counterion identified as $X^-$, where said counterion is halide, $BF_4^-$, $CH_3C_6H_4SO_3^-$, $C_6H_5SO_3^-$, $CH_3SO_3^-$, $CF_3SO^-$, $PO_4^-$, phosphonate of the formula $(R^1O)_2P(O)O^-$ where $R^1$ is an alkyl or aryl group, a group of the formula $(OR^1)PO^-$ where $R^1$ is an alkyl or aryl group, and a group of the formula $(R^2)_2(O)PO^-$, where $R^2$=OR, O-aryl, $NR_2$, and SR.

The present invention comprises a process for preparing a compound of the formula I as illustrated below in the Examples. The stereochemical representations depict the preferred stereoisomers. The process can be carried out using a non-chiral aziridinium salt, in which case the stereochemical representations designate the preferred isomers having the relative stereochemistry shown. Alternatively, the process can utilize a single enantiomeric aziridinium salt to produce a single enantiomer of compound I, wherein the stereochemical representations further designate absolute stereochemistry.

While the preferred reagents and reaction conditions for the various steps are described in detail in the Examples section, the following summarizes the details.

The process starts with the conversion of the hemitartrate salt of the formula VI to the amino alcohol of formula VII. The compound of formula VI is dissolved, suspended or dispersed in a suitable solvent, water and sodium chloride. Examples of suitable solvents are ketone, ester, ether, hydrocarbon and mixtures thereof. More specific examples of suitable solvents include toluene, xylene, tetrahydrofuran, methyl-t-butylether, ethyl acetate, methyl ethyl ketone, dichloromethane. A preferred solvent is methyl-t-butylether.

A basic compound, for example, ammonium hydroxide, is added to the mixture until the mixture is basic, i.e., pH>about 8. Alternatively, the compound of formula VI is treated with the basic compound, toluene and water. Examples of a suitable basic compound are a metal hydroxide, oxide, carbonate and bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium; or a metal salt of a $C_1$–$C_{12}$ alkanol, a $C_3$–$C_{12}$ cycloalkanol, a ($C_3$–$C_8$ cycloalkyl)$C_1$–$C_6$ alkanol; ammonia; a $C_1$–$C_{12}$ alkylamine, a di($C_1$–$C_{12}$ alkyl) amine, a $C_3$–$C_8$ cycloalkylamine, a N—($C_3$–$C_8$ cycloalkyl)-N—($C_1$–$C_{12}$ alkyl)amine. a di($C_3$–$C_8$ cycloalkyl)amine, a ($C_3$–$C_8$ cycloalkyl)$C_1$–$C_6$ alkylamine, a N—($C_3$–$C_8$-cycloalkyl)$C_1$–$C_6$-alkyl-N—($C_1$-$Cl_2$ alkyl)amine, a N—($C_3$–$C_8$ cycloalkyl)$C_1$–$C_6$ alkyl-N—($C_3$–$C_8$ cycloalkyl) amine, a di[($C_1$–$C_6$ cycloalkyl)$C_1$–$C_6$ alkyl]amine and a heterocyclic amine selected from the group consisting of imidazole, triazole, pyrrolidine, piperidine, heptamethyleneimine, morpholine, thiomorpholine and a 1-($C_1$–$C_4$ alkyl)piperazine. Preferred basic compounds are ammonium hydroxide, KOH, NaOH, $Na_2CO_3$, $K_2CO_3$, $K_2CO_3$, $NaHCO_3$, $KHCO_3$, tetramethylguanidine, 1,8-diazabicyclo[5.4.0]undec-7-ene(DBU), diisopropylethylamine and mixtures thereof. A particularly preferred basic compound is ammonium hydroxide. The compound of formula VII is isolated by suitable means such as, for example, distillation in a manner well known to those skilled in the art. The aqueous layer is removed and diglyme is added.

Next, the amino alcohol of formula VII is alkylated with a compound of the formula $J$-$CH_2$-$Q$ to form the compound of formula VIII, where J is —Cl, —Br, —I, —$OSO_2CH_3$, —$OSO_2CF_3$, —$OSO_2C_6H_4CH_3$, phosphate, phosphite or phosphonate, and Q has the formula

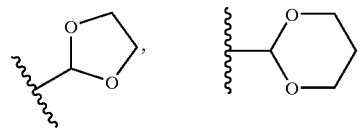

or —$CH(OR)_2$, where R is $C_1$–$C_6$ alkyl. Preferably Q is —$CH(OCH_3)_2$. A suitable base may be added. In an illustrative preparation, anhydrous potassium carbonate and bromoacetaldehyde dimethyl acetal are added to the reaction mixture. Examples of suitable solvents are listed above. Preferred solvents are methyl-t-butylether and toluene. The compound of formula VIII is isolated by extracting it with the solvent.

The compound of formula VIII is treated with an aziridinium forming reagent and a suitable base, in a solvent to form the intermediate compound of formula II. Examples of suitable bases and solvents are listed above. A preferred solvent is THF and a preferred base is an alkyllithium. Preferred alkyllithiums include n-butyllithium or hexyllithium. The aziridinium forming reagent is selected from a group of reagents that form an aziridinium group, said reagent containing a halophosphate, halophosphite, pyrophosphate, phosphoramidate, phosphorite, phosphate, phosphonate of the formula $(R^1O)_2P(O)O^-$ where $R^1$ is an alkyl or aryl group, a group of the formula $(OR^1)PO^-$ where $R^1$ is an alkyl or aryl group, and a group of the formula $(R^2)_2(O)PO^-$, where $R^2$=OR, O-aryl, $NR_2$, and SR. Preferred aziridinium forming reagents are diphenyl chlorophosphate or diphenyl phosphoryl chloride. The compound of formula II may reversibly co-exist with the amines of formulas IX and X. However, upon continuation of the reaction of the compound of formula II with the compound of formula III in the next step, any remaining compounds of formulas IX and X get converted back to the compound of formula II in its ongoing reaction with the compound of formula III. The intermediate of formula II is subsequently treated as described below.

The compound of formula II is reacted with an organometallic reagent (formula III) and a metal salt (preferably a copper salt) or a copper salt-lithium chloride complex of $CuZ_n \cdot dLiCl$, where Z, n and d are defined above, to form a reaction product of formula XV

XV

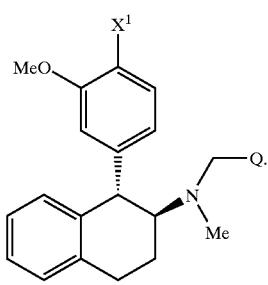

The copper salt is preferably of the formula $CuZ_m$, (m is defined above) where Z is cyanide, halide, acetate, acetyl acetonate, benzoyl benzoate, trifluoroacetate, thiophenoxide, phenylacetylide, thiocyanate, tetrafluoroborate, trifluoromethanesulfonate or trifluoroacetylacetonate, preferably cyanide. The organometallic reagent is of formula III

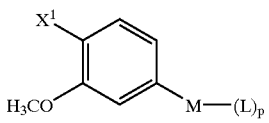

where $X^1$ is Cl or F, where M may be Li, Co, Ni, Mg, Zn, Ti, Ce, Mn and Cu; and L may be Br, Cl, CN, acetate and acetyl acetate, p being a number ranging from 1 to 3 depending on the valence of the metal M. A preferred organometallic reagent is

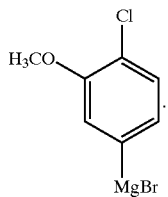

The reaction product of formula II and the organometallic reagent (formula III) is converted into an acid salt of formula IV, such as an oxalate, tartarate, citrate, malonate and the like. This acid salt is created by reacting said reaction product with the appropriate acid (e.g., oxalic acid, tartaric acid, malonic acid, citric acid and the like) to form the acid salt compound of formula IV. Preferably, the acid used is of the formula HY where Y is oxalate, i.e., oxalic acid. The compound of formula IV can be isolated by procedures such as filtration, drying, solvent extraction and the like, well known to those skilled in the art.

In an alternative embodiment, the compound of formula X reacts with the compound of formula III to produce the compound of formula IV.

The compound of formula IV is cyclized and reduced to form the compound of formula V. An acid (preferably methanesulfonic acid) is added to the salt of formula IV, followed by subsequent addition of methyl-t-butylether and butyl t-butylamine borane. The product is isolated by procedures such as filtration, solvent extraction and the like, and is then converted into an acid salt (formula V), such as oxalate, malonate, tartarate, citrate and the like, by reacting with the appropriate acid (e.g., oxalic acid, malonic acid, tartaric acid and citric acid and the like).

The compound of formula V is subsequently deprotected (i.e., removing the methyl from methoxy) to form the desired compound of formula I which may be washed and extracted with solvent and isolated by procedures well known to those skilled in the art such as solvent extraction, filtration, distillation and the like.

The products of the various steps in the reaction schemes described herein may be isolated and purified by conventional techniques such as, for example, filtration, re-crystallization, solvent extraction, distillation, precipitation, sublimation and the like, well known to those skilled in the art. The products may be analyzed and/or checked for purity by conventional methods well known to those skilled in the art such as, for example, thin layer chromatography, NMR, HPLC, melting point, mass spectral analysis, elemental analysis and the like.

The following non-limiting EXAMPLES are provided in order to further illustrate the present invention.

EXAMPLES

Unless otherwise stated, the following abbreviations have the stated meanings in the Examples below:

HPLC=High Performance Liquid Chromatography
M.pt=melting point
NMR=nuclear magnetic resonance spectroscopy
MS=mass spectral analysis
mL=milliliters
g=grams
rt=room temperature (ambient) about 25° C.
Boc (or t-Boc)=tert-butoxycarbonyl
MAT=(+)-(1R, 2R)-trans-1,2,3,4-tetrahydro-1-(methylamino)2-naphthalenol hemitartrate
THF=tetrahydrofuran Example 1

Preparation of (+)-(1R, 2R)-trans-1,2,3,4-tetrahydro-1-[(2,2-dimethoxyethyl)methylamino]2-naphthalenol.

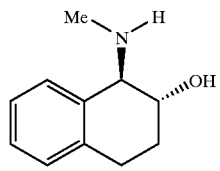

This preparation is comprised of i) generation of the amino alcohol, ii) alkylation of this amino alcohol and iii) isolation of the product.

Generation of the Amino Alcohol from its Salt:

This was achieved via one of the following two methods:

Method 1:

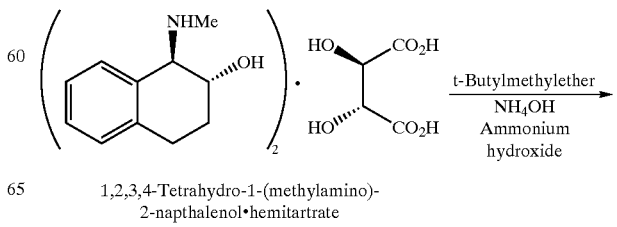

1,2,3,4-Tetrahydro-1-(methylamino)-2-napthalenol•hemitartrate

-continued

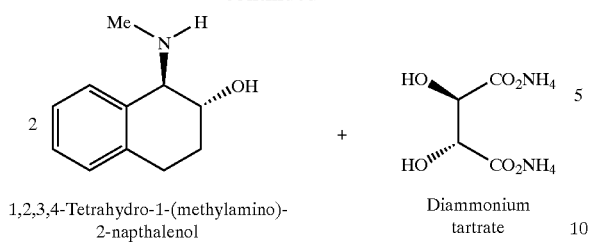

1,2,3,4-Tetrahydro-1-(methylamino)-
2-napthalenol

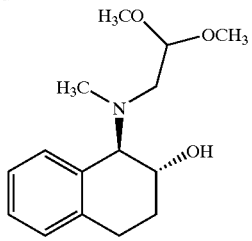

Diammonium
tartrate

To a mixture of methyl-t-butylether, water, sodium chloride and (+)-(1R, 2R)-trans-1,2,3,4-tetrahydro-1-(methylamino)2-naphthalenol hemitartrate (MAT), ammonium hydroxide was added until the water layer remained basic (pH>8) and a clear solution resulted. The resultant layers were separated. The aqueous layer was extracted with methyl-t-butylether and the layers separated again. The organic layers were combined and distilled to twice the volume of MAT charged. Diglyme was charged (twice the volume of MAT). This solution was distilled to remove methyl-t-butylether and then a gentle vacuum was applied to remove most of the remainder of methyl-t-butylether.

Method 2:

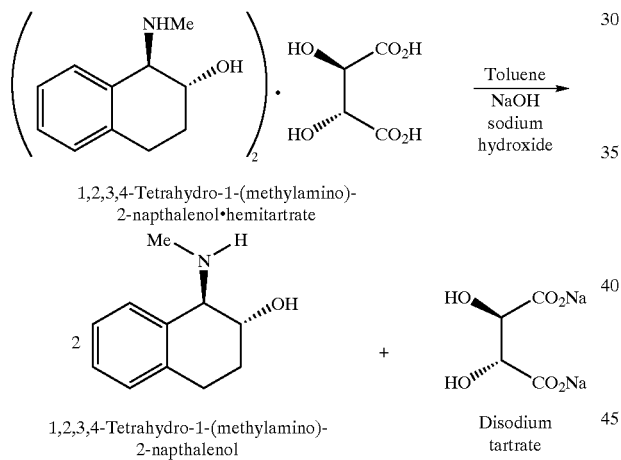

1,2,3,4-Tetrahydro-1-(methylamino)-
2-napthalenol•hemitartrate 1,2,3,4-Tetrahydro-1-(methylamino)-
2-napthalenol Disodium
tartrate Aq. NaOH was added to a mixture of MAT, toluene and water and stirred until a clear solution resulted. The aqueous layer was removed and diglyme was added. The toluene was removed via vacuum distillation. The heated mixture was cooled to ~80° C., and a gentle vacuum was applied to remove the remainder of toluene.

Alkylation of the Amino Alcohol:

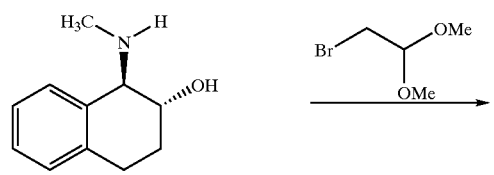

-continued

To the stirred solution obtained from either of the above processes, excess powdered anhydrous potassium carbonate and bromoacetaldehyde dimethyl acetal were added. The reaction mixture was stirred and heated gradually to 125–130° C. and then held at 130° C. until the reaction was complete. Additional reagents could have been added to complete the reaction faster.

Isolation of the Product:

This was achieved via one of the following two methods.

Method 1: The mixture was cooled to room temperature and the solids were filtered. The solids and the reaction flask were washed with two portions of methyl-t-butylether. The filtrates were combined, 1N sulfuric acid was added to achieve an acidic pH and the mixture was stirred at room temperature. The lower aqueous layer was separated and the organic layer was extracted with 1N sulfuric acid. NaCl was added to the aqueous layer. The mixture was stirred and then extracted with methyl-t-butylether twice. The organic layer was atmospherically distilled and the liquid was saved for further reaction.

Method 2: The mixture was cooled to room temperature and the solids filtered. The solids were washed with toluene. The filtrates were combined and distilled under vacuum toluene with the left over bromoacetaldehyde dimethyl acetal. Typical yield by HPLC was 90–92% (product in diglyme): MS: 266 (M+H).

Preparation of (+)-(1S, 2S)-trans-1-(4-chloro-3-methoxyphenyl)-N-(2,2-dimethoxyethyl)-1,2,3,4-tetrahydro-N-methyl-2-naphthaleneamine oxalate (1:1).

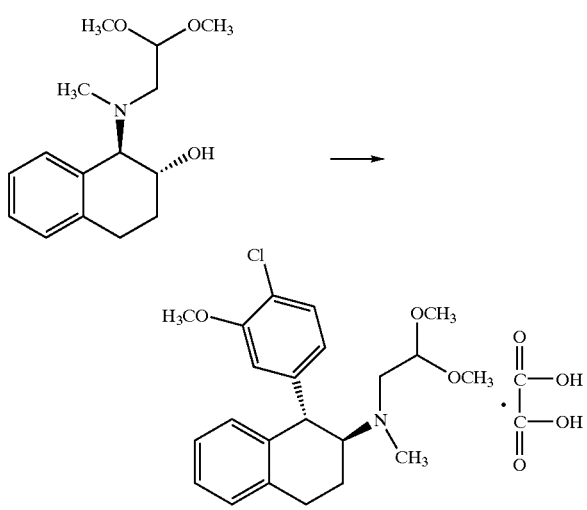

Procedure A. Anhydrous THF was added to a dry solution of (+)-(1R, 2R)-trans-1,2,3,4-tetrahydro-1-[(2,2-dimethoxyethyl) methylamino]2-naphthalenol in diglyme followed by a small amount 1,10-phenanthroline and cooled to −15° C. The reaction mixture was kept below −15° C. 2.5 M solution of n-Butyl lithium in hexanes was added until the reaction mixture turned red in color. A solution of p-toluenesulfonyl chloride in dry THF was added while stirring reaction mixture at a temperature between −25 to −30° C. The reaction mixture was stirred at −20° C. and it was subsequently cooled to −25° C. Under inert conditions, a catalytic amount of copper (I) cyanide in THF was added. The mixture was stirred and excess 3-methoxy-4-chlorophenyl magnesium bromide in THF was added to allow the reaction mixture to warm up (~−5 ° C.). After the addition, the reaction mixture was heated to 40–45° C. and held at that temperature for 1–2 hours. The reaction mixture was then cooled to 0° C. Aqueous ammonium chloride solution was added to allow the reaction mixture to attain room temperature. The organic layer was separated and washed with aqueous ammonium chloride solution and separated again. The combined aqueous layers were extracted with methyl-t-butylether. The organic layers were combined. The product was extracted with 1 N sulfuric acid (acidic pH), the aqueous layer was separated and it was re-extracted with 1 N sulfuric acid. Methyl-t-butylether was added to the combined aqueous layers and the pH was adjusted to 5.5–6.0 with ammonium hydroxide. The organic layer was separated and the aqueous layer was re-extracted with methyl-t-butylether while a pH of 5.5–6.0 was maintained with ammonium hydroxide. The combined organic layers were distilled to remove methyl-t-butylether.

Isopropanol was added to the mixture. The solution was filtered and warmed to 40° C. To this mixture, a solution of oxalic acid dihydrate in isopropanol was added and the mixture was kept at 45° C. The stirred mixture was gradually cooled to room temperature. The mixture was seeded and stirred at room temperature. The mixture was cooled to 0° C. and filtered. The resultant cake was washed with ice-cold isopropanol followed by ice-cold methyl-t-butylether. The solid was dried resulting in a 60–70% yield. MS(FAB): 390, 391, 392.

Procedure B. To a dry solution of (+)-(1R,2R)-trans-1,2,3,4-tetrahydro-1-[(2,2-dimethoxyethyl)methylamino]2-naphthalenol in diglyme, dry THF was added, followed by a small amount of 1,10-phenanthroline. The mixture was cooled to −15° C. The reaction mixture was kept below −15° C. Subsequently, 2.5M solution of hexyl-lithium in hexanes was added until the reaction mixture turned red in color. The reaction mixture was cooled to −15° C. and stirred. Diphenyl chlorophosphate was added while maintaining a temperature of between −20 to −30° C.

A solution of excess 3-methoxy-4-chlorophenyl magnesium bromide in THF was separately mixed with a catalytic amount of CuCl.2LiCl in anhydrous THF at room temperature. This solution was stirred and maintained at a temperature of ~30–35° C. by the slow addition of the cold solution prepared above. After the addition, the mixture was warmed to 40–45° C. and held at that temperature for 1–2 h. It was then cooled to 0° C. and aqueous ammonium chloride solution was added. The reaction mixture was allowed to attain room temperature. The organic layer was separated and washed with aqueous ammonium chloride solution and the layer was separated again. The aqueous layers were combined and later extracted with methyl-t-butylether. The combined organic layers were washed with NaOH, followed by brine solution. The organic layer was distilled to remove methyl-t-butylether. Methyl-t-butylether was added once again. The mixture was filtered and it was subsequently combined with isopropanol and warmed to 40° C. A solution of oxalic acid dihydrate in isopropanol was added and the mixture was kept at 45° C.

The stirred mixture was gradually cooled to room temperature. (If necessary, a seeding process could have been done). The mixture was stirred at room temperature. It was cooled to 0° C. and filtered. The cake was washed with ice-cold isopropanol followed by ice-cold methyl-t-butylether. The solid was dried to produce a yield of 70%–85%.

Similarly, a combination of 5 mol % CuCN.2LiCl and diphenyl chlorophhosphate gave about an isolated 70–85% yield.

Preparation of trans-(−)-(6aS,13bR)-11-chloro-6,6a,7,8,9,13b-hexahydro-12-methoxy-7-methyl-5H-benzo[d]naphth[2,1-b]azepine, malonate (1:1)

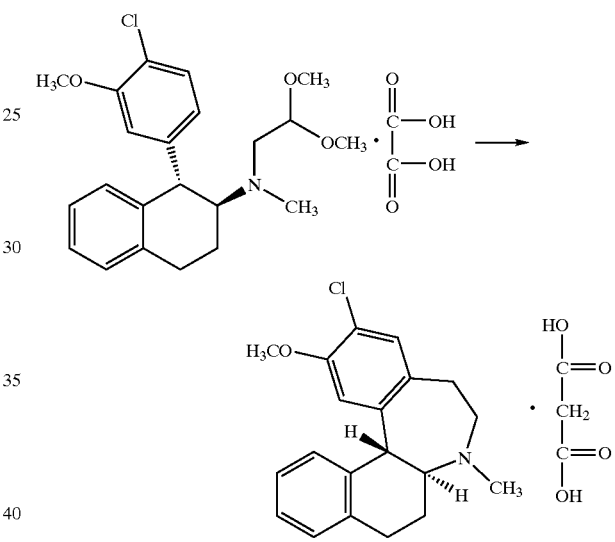

Methanesulfonic acid was stirred at room temperature and slowly added to the salt from the above reaction, with the reaction temperature kept below 45–50° C. The reaction mixture was warmed to 55–60° C. after the addition and this temperature was maintained until complete consumption of the starting material. The reaction mixture was cooled to 0° C., and the reaction temperature kept below 15° C. Methyl-t-butyl ether was added followed butyl t-butylamine borane. The reaction mixture was cooled and stirred. This reaction mixture was kept below 15° C. and water was slowly added followed by aq. potassium hydroxide solution to a reach basic pH. The aqueous layer was separated, and it was extracted twice with methyl-t-butylether. The organic layers were combined, washed with water and then the organic layer was distilled atmospherically. Isopropanol was added, distilled atmospherically and kept at 40–45° C. A warm solution of malonic acid in isopropanol was added to the reaction mixture. The mixture was allowed to attain room temperature slowly and it was cooled to 0° C. for 1 h. The product was filtered and washed with ice cold isopropanol followed by ice cold methyl-t-butylether. The product was dried to obtain 92% yield; MS(FAB): 330, 329, 328, 327.

Purification procedure: trans-(−)-(6aS,13bR)-11-chloro-6,6a,7,8,9,13b-hexahydro-7-methyl-5H-benzo[d]naphth[2,1-b]azepine-12-ol, hydrochloride (1:1)

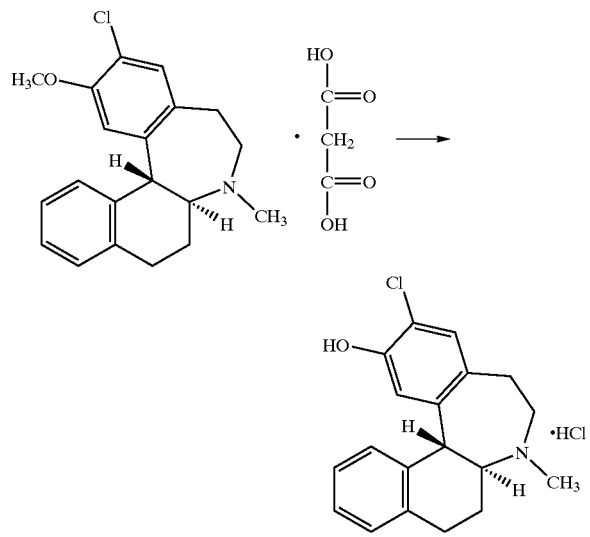

To a stirred mixture of the malonate salt from the above procedure, in 1:1 toluene and water, aqueous NaOH solution was added. The stirred mixture was maintained at 40–50° C. to obtain a biphasic solution. The mixture was cooled to room temperature, the organic layer was separated and the aqueous layer was extracted with toluene. The combined organic layers were washed with water. The organic layer was concentrated until the water content of this solution was below 0.1%. Boron trichloride was added to the resultant stirred solution at room temperature and then the mixture was heated to about 70° C. to ensure maximum demethylation.

This reaction mixture was slowly added to stirred methanol held at 25° C. After the exothermic quench, the reaction mixture was concentrated and cooled so that the resultant suspension reached room temperature. Methyl-t-butylether was added and the mixture was cooled to 0–5° C. and filtered. The solid was washed with a mixture of cold methanol/methyl-t-butylether followed by cold methyl-t-butylether, and then dried to obtain a solid in 90–95% yield. This solid was dissolved in refluxing methanol and cooled to room temperature. Methyl-t-butylether was added and the solid was cooled to −20° to −30° C. to obtain 94–98% recovery of the title compound as a white solid. MS: 317, 316, 315, 314.

EXAMPLE 2

The Formation of Amines of Formulas IX and X

The stepwise conversion of the compound of formula XI into the mixture of chloramines (compounds of formulas IX and X) (scheme 2) was studied using the NMR spectroscopy. A sample of pure compound of formula XI was dissolved in THF-$d_4$ in an NMR tube, several crystals of phenantroline indicator were added and reaction was cooled to −50° C. A solution of HexLi in hexanes (1.05–1.1 eq) was added dropwise until the color endpoint was obtained indicating that the formation of lithium alkoxide is complete. Neat DPCP (diphenyl chlorophosphate) (1.1 equiv) was then charged maintaining the reaction temperature below −40° C. Once the complete formation of the compound of formula XII was ascertained, the reaction was gradually warmed up to room temperature and $^1H$, $^{13}C$ and $^{31}P$ NMR were taken in 10 min time intervals.

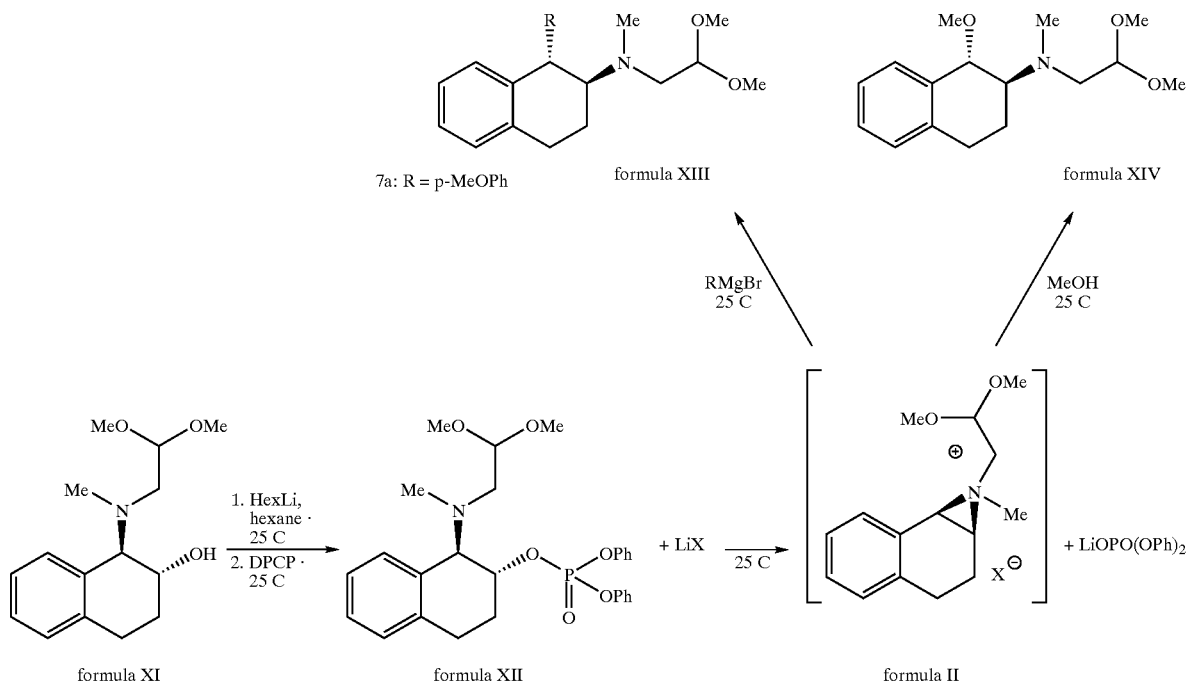

Scheme 2

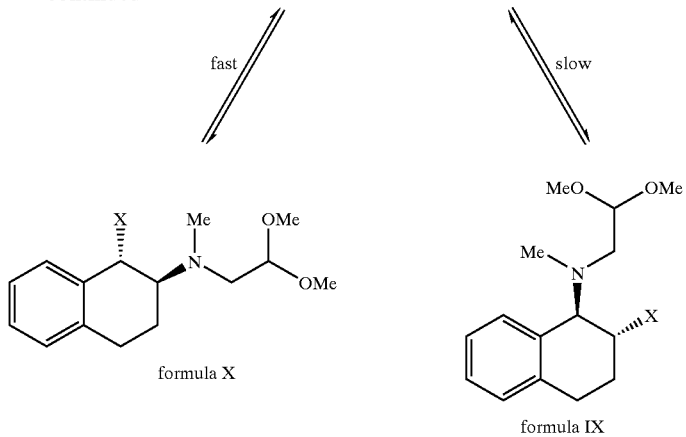

formula X formula IX

At −40° C., ³¹P NMR indicated rapid consumption of DPCP (−1.5 ppm rel. to H₃PO₄) and formation of a predominantly single species (doublet at −7.6 ppm, J=6.5 Hz) with chemical shift close to that of diphenylphosphate HOP(O)(OPh)₂(−6.8 ppm). In ¹³C NMR, downfield shift of CHOH carbon signal by 6 ppm and splitting of CHOH (J=6.5 Hz) and CHN (J=7.7 Hz) carbon signals on phosphorus was observed. In ¹H NMR, downfield shifts of CHOH proton by 1.4 ppm and CHN proton by 0.37 ppm were observed. These spectral data were consistent with the proposed formation of phosphate intermediate of formula XII. Once formed, the phosphate of formula XII was found to be quite stable at temperatures below −20° C.

Upon the gradual warm up of reaction mixture to 25° C., the original phosphate peak of the phosphate of formula XII disappeared and a new signal at −6.1 ppm appeared in ³¹P NMR. In ¹³C NMR, loss of phosphorus coupling and upfield shift of CHOH carbon signal was observed. Two different species whose spectra are consistent with chloramines of formulas IX and X (major: 68.2, 61.2, 57.6, 53.9 ppm; minor: 70.7, 59.3, 58.3, 53.1 ppm) could be clearly detected in reaction mixture. Inspection of ¹H and ¹³C NMR spectra of the reaction mixture taken at different temperatures and comparison to the spectra of authentic aziridinium tetrafluoroborate confirmed the absence of any detectable quantitities of aziridinium ion intermediate. After ageing the reaction mixture at 25° C. for several days, ¹H and ¹³C NMR indicated almost complete rearrangement of the initially major chloramine into the minor isomer. These results are consistent with the findings of other workers in structurally similar pseudoephedrin and ephedrin systems (K. Dieter et al) where alpha-chloramine was shown to be the initially formed product which then slowly rearranged into the more stable beta-chloramine. The identity of labile chloramine isomers of formula IX and X in reaction solution was further ascertained by LCMS (M+H m/z 284, 252, 216, 165,129) and HRMS (calcd. for M+H, C₁₅H₂₃ClNO₂ 284.1417, found 284.1411) analysis.

It will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A process for preparing a compound of formula I:

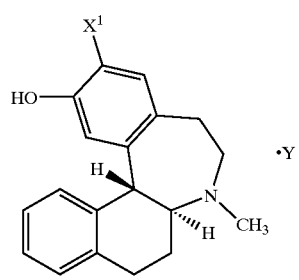

where X¹ is Cl or F and Y is selected from the group consisting of malonic, acid, oxalic acid, sulfonic acid, phosphoric acid hydrochloride from compound of formula II:

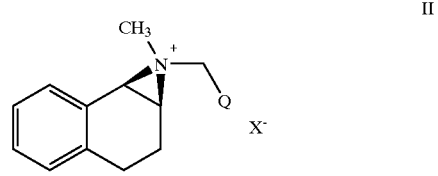

where Q has the formula

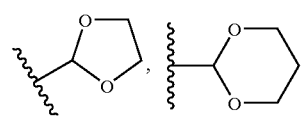

or —CH(OR)₂, where R is C₁–C₆ alkyl and wherein X is an anion selected from the group consisting of:

phosphonate of the formula (R¹O)₂P(O)O⁻ where R¹ is an alkyl or aryl group, a group of the formula (OR¹)PO⁻ where R¹ is an alkyl or aryl group, and a group of the formula (R²)₂(O)PO⁻, where R²=OR, O-aryl, NR₂, and SR: said process comprising:

(a) reacting the compound of formula II with an organometallic reagent of formula III:

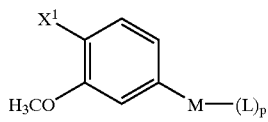

where $X^1$ is Cl or F, where M is selected from the group consisting of Co, Ni, Mg, Zn, Ti, Ce, Mn and Cu; and L is selected from the group consisting of Br, Cl, CN, and acetate, p being a number ranging from 1 to 3 depending on the valence of M;

in the presence of a metal salt of the formula $CuZ_m$ (m is 1 or 2) or in the presence of a copper salt-lithium chloride complex of formula, $CuZ_n \cdot dLiCl$ (n is 1 or 2, d ranges from 1 to 4), where Z is selected from the group consisting of cyanide, halide, acetate, acetyl acetonate, benzoyl benzoate, trifluoroacetate, thiophenoxide, phenylacetylide, thiocyanate, tetrafluoroborate, trifluoromethanesulfonate and trifluoroacetylacetonate, followed by treatment with acid Y, to form a compound of formula IV:

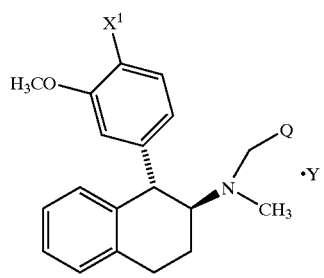

where $X^1$ and Y are as defined as above;

b) cyclizing and reducing the compound of formula IV to form a compound of formula V;

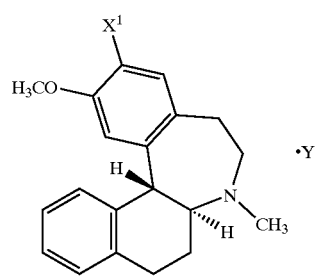

and (c) deprotecting the compound of formula V to form the compound of formula I
  (i) wherein the compound of formula V is washed with an organic solvent, water and a base to obtain a biphasic solution wherein said biphasic solution contains an organic and an aqueous layer;
  (ii) wherein said organic layer is separated from the aqueous layer;
  (iii) boron trichloride is added to said organic layer and then subsequently heated then quenched;
  (iv) wherein the quenched solution of step (iii) is concentrated, cooled, washed with an organic solvent and filtered to obtain a solid containing the compound of formula I.

2. The process of claim 1 wherein Y is an oxalic acid or malonic acid, X is an anion selected from the group consisting of:
  phosphonate of the formula $(R^1O)_2P(O)O^-$ where $R^1$ is an alkyl or aryl group,
  a group of the formula $(OR^1)PO^-$ where $R^1$ is an alkyl or aryl group, and
  a group of the formula $(R^2)_2(O)PO^-$, where $R^2$=OR, O-aryl, $NR_2$, and SR:
  Q is —$CH(OCH_3)_2$,
  R is methyl,
  M is Mg,
  Y is oxalic in step (a),
  Y is malonic in step (b),
  p is 1, and
  said metal salt is CuCN.

3. The process of claim 1 wherein Y is an oxalic acid or malonic acid,
  Q is —$CH(OCH_3)_2$,
  R is methyl,
  M is Mg,
  Y is oxalic in step (a),
  Y is malonic in step (b),
  p is 1, and
  said cooper salt-lithium chloride complex is CuCl.2LiCl.

4. The process of claim 2 or 3 wherein the organometallic reagent is a compound of the formula

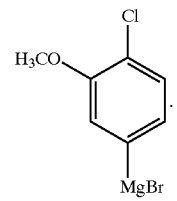

5. The process of claim 1 where the compound of formula II is prepared by a process comprising:
  (a) treating a compound of formula VI

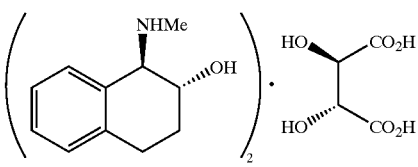

with a base to form a compound of formula VII:

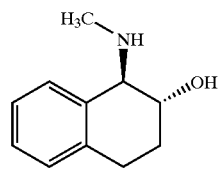

(b) alkylating the compound of formula VII with a compound of the formula J-$CH_2$-Q, where J is selected from the group consisting of —Cl, —Br, —I, —$OSO_2CH_3$, —$OSO_2CF_3$, —$OSO_2C_6H_4CH_3$, phosphate, phosphite and phosphonate, and Q is as defined in claim 1, to form a compound of formula VIII:

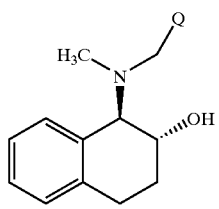

VIII and (c) reacting the compound of formula VII with a base and an aziridinium forming reagent containing a halophosphate, halophosphite, phosphoramidate, pyrophosphate, phosphorite, phosphate, phosphonate of the formula $(R^1O)_2P(O)O^-$ where $R^1$ is an alkyl or aryl group, a group of the formula $(OR^1)PO^-$ where $R^1$ is an alkyl or aryl group, and a group of the formula $(R^2)_2(O)PO^-$, where $R^2$=OR, O-aryl, $NR_2$, and SR, to form the compound of formula II.

6. The process of claim 5 wherein Q is —$CH(OCH_3)_2$ and J is selected from the group consisting of Cl, Br, I, —$OSO_2CH_3$ and —$OSO_2C_6H_4CH_3$.

7. The process of claim 6 wherein the base in step (c) is an alkyllithium.

8. The process of claim 7 wherein a solvent is used in step (a) to dissolve the compound of formula VI.

9. The process of claim 8 wherein said solvent is selected from the group consisting of a hydrocarbon, ether, alcohol, ketone, ester and mixtures thereof.

10. The process of claim 9 wherein said solvent is selected from the group consisting of THF, diglyme, methyl t-butylether, toluene, xylene and mixtures thereof.

11. The process of claim 10 wherein said solvent is methyl t-butylether.

12. The process of claim 11 wherein the aziridinium forming reagent is diphenyl chlorophosphate or diphenyl phosphoryl chloride.

13. The process of claim 12 wherein the base is n-butyllithium or hexyllithium.

14. The process of claim 13 wherein step (c) is performed at a starting temperature of about −40° C. and is heated to a final temperature of about 80° C.

15. The process of claim 14 wherein step (c) is performed at a starting temperature of about −30° C. and is heated to a final temperature of about 55° C.

16. The process of claim 15 wherein step (c) is performed at a starting temperature of about −20° C. and is heated to a final temperature of about 0° C.

17. The process of claim 4 wherein the cyclization of formula IV in step (b), occurs in the presence of $MeSO_3H$, and said reduction is performed with a metal hydride reducing agent or a borane amine complex.

18. The process of claim 17 wherein the metal hydride reducing agent is selected from the group consisting of $NaBH_4$, $NaBH_3CN$, $LiBH_4$ and $LiAlH_4$.

19. The process of claim 17 wherein the borane amine complex is selected from the group consisting of borane-methylamine, borane-tert-butylamine, borane-piperidine, borane-triethylamine, borane-N,N-diisopropylethylamine, borane-N,N-diethylaniline, borane-morpholine, borane-4-ethylmorpholine and borane-4-pheylmorpholine complex.

20. The process of claim 19 wherein the borane amine complex is borane-tert-butylamine.

* * * * *

UNITED STATES PATENT AND TRADEMARK OFFICE
CERTIFICATE OF CORRECTION

PATENT NO. : 6,875,866 B2
DATED : April 5, 2005
INVENTOR(S) : Dahanukar et al.

Page 1 of 1

It is certified that error appears in the above-identified patent and that said Letters Patent is hereby corrected as shown below:

Column 20,
Line 38, change "malonic, acid" to -- malonic acid --.
Line 39, insert the word -- and -- between the words "acid" and "hydrochloride".

Column 21,
Lines 17-18, delete the words "acetyl acetonate,".

Column 22,
Line 13, insert the word -- acid -- between the words "oxalic" and "in".
Line 14, insert the word -- acid -- between the words "malonic" and "in".
Line 22, insert the word -- acid -- between the words "oxalic" and "in".
Line 23, insert the word -- acid -- between the words "malonic" and "in".

Column 23,
Line 15, change "VII" to -- VIII --.

Column 24,
Line 29, change "pheylmorphollne" should read -- phenylmorpholine --.

Signed and Sealed this

Fifth Day of July, 2005

JON W. DUDAS
*Director of the United States Patent and Trademark Office*